US00PP24437P3

(12) United States Plant Patent
Harris

(10) Patent No.: US PP24,437 P3
(45) Date of Patent: May 13, 2014

(54) SHRUB ROSE PLANT NAMED 'HARPBALLRED'

(50) Latin Name: *Rosa hybrida*
Varietal Denomination: Harpballred

(75) Inventor: Peter G. Harris, Charleston, WV (US)

(73) Assignee: CP Delaware, Inc., Wilmington, DE (US)

( * ) Notice: Subject to any disclaimer, the term of this patent is extended or adjusted under 35 U.S.C. 154(b) by 81 days.

(21) Appl. No.: 13/573,302

(22) Filed: Sep. 10, 2012

(65) Prior Publication Data

US 2014/0075607 P1 Mar. 13, 2014

(51) Int. Cl.
*A01H 5/00* (2006.01)

(52) U.S. Cl.
USPC ..... Plt./108

(58) Field of Classification Search
CPC ..... A01H 5/0222
USPC ..... Plt./105
See application file for complete search history.

*Primary Examiner* — Annette Para
(74) *Attorney, Agent, or Firm* — Buchanan, Ingersoll & Rooney, PC

(57) ABSTRACT

A new and distinct shrub rose plant is provided that abundantly forms in clusters attractive small cup-like bright red blossoms with a white eye that drop their petals well upon full maturity. The plant exhibits vigorous vegetation and a mounding growth habit. The foliage is dark green with a glossy finish on the upper surface. The plant is well suited for growing as attractive ornamentation in the landscape. The plant is particularly well suited for growing in smaller areas as a ground cover or as a mass planting. Alternatively, the plant can be grown in containers.

1 Drawing Sheet

Botanical/commercial classification: *Rosa hybrida*/Shrub Rose Plant.

Varietal denomination: cv. Harpballred.

SUMMARY OF THE INVENTION

The new variety of *Rosa hybrida* landscape shrub rose plat of the present invention was created at Charleston, W. Va., U.S.A., by open pollination in a rose garden setting at my home in the hope that desired characteristics would be displayed in the progeny. The female parent (i.e., the seed parent) was the 'Ballerina' variety (non-patented in the United States). The male parent (i.e., the pollen parent) is unknown. The pollen may have been derived from the 'Ballerina' variety. The parentage of he new variety can be summarized as follows:

'Ballerina'×Unknown.

The seeds resulting from the above pollination were sown during 1997 and small plants were obtained which were physically and biologically different from each other. Selective study resulted in the identification during 1998 of a single plant of the new variety.

It was found that the new Landscape Shrub rose plant of the present invention possesses the following combination of characteristics:

(a) abundantly forms in clusters attractive small single cup-like bright red blossoms with a white eye that drop their petals well upon full maturity,
(b) exhibits a mounding growth habit,
(c) forms vigorous vegetation,
(d) forms attractive dark green foliage with a glossy upper surface, and,
(e) is well suited for growing as attractive ornamentation in the landscape.

A new rose variety is provided which bears attractive single very small brightly colored blossoms combined with attractive dark green foliage. The blossom coloration contrasts well with the dark green foliage.

The new variety well meets the needs of the horticultural industry. It can be grown to advantage as ornamentation in parks, gardens, public areas, and in residential settings. The new variety is particularly well suited for growing in smaller areas as a ground cover or as a mass planting. The new variety also grows well in containers.

The new variety of the present invention can be readily distinguished from its 'Ballerina' parent as well as from other Polyantha hybrid varieties, such as the 'Radcleome' variety (U.S. Plant patent application Ser. No. 13/507,959, filed Aug. 9, 2012). More specifically, the 'Ballerina' female parent forms dissimilar pink blossoms with white centers. The 'Radcleome' variety has a significantly taller stature and forms dissimilar medium pink finishing to light pink blossoms.

The characteristics of the new variety have been found at Wasco, Calif., U.S.A., and near West Grove, Pa., U.S.A., to be homogeneous and stable and to be strictly transmissible by asexual propagation, such as the rooting of cuttings, from one generation to another. The new variety reproduces in a true-to-type manner by such asexual propagation.

The new variety has been named 'Harpballred', and is being marketed under the LOOK-A-LIKES and HYDRANGEALICIOUS trademarks.

BRIEF DESCRIPTION OF THE PHOTOGRAPH

The accompanying photograph shows, as nearly true as it is reasonably possible to make the same in a color illustration of this character, typical flowering rose plants of the new variety. The illustrated rose plants of the new variety were approximately three years of age and were observed during June while growing outdoors on their own roots near West Grove, Pa., U.S.A.

DETAILED DESCRIPTION

The chart used in the identification of colors is that of The Royal Horticultural Society (R.H.S. Colour Chart—1995 Edition or equivalent), London, England. The description is based on the observation of two-year-old specimens of the new variety during June while growing in a greenhouse on their own roots near West Grove, Pa., U.S.A.

Class: Landscape Shrub Rose, Polyantha Hybrid.

Plant:

*Height*.—Approximately 2 feet on average at full maturity.

*Width*.—Approximately 2½ to 3 feet on average a full maturity.

*Habit*.—Mounding.

Branches:

*Color*.—Near Yellow-Green Group 144B on young stems, and Greyed-Orange Group 177A on adult wood.

*Texture*.—Generally smooth on young stems and somewhat rough on adult wood.

*Thorns*.—Size: commonly approximately 3 mm in length on average. Quantity: numerous. Color: commonly near Yellow-Green Group 144A overlaid with Greyed-Purple Group 184B on young stems, and near Greyed-Orange Group 166B overlaid with Greyed-Orange Group 166A at the apex.

Leaves:

*Size*.—Commonly approximately 8 cm in length on average and approximately 7 cm in width on average for a five-leaflet leaf.

*Leaflets*.—Number: 3, 5, and 7. Length: approximately 4 cm on average for a terminal leaflet, and approximately 3.4 cm on average for a lower leaflet. Width: approximately 2 cm on average for a terminal leaflet, and approximately 1.6 cm on average for a lower leaflet. Shape: ovate. Margins: serrate. Texture: generally smooth on the upper and under surfaces. Overall appearance: attractive dark green leaves with a glossy upper surface. Color: (when young): upper surface: near Yellow-Green Group 144A. under surface: near Yellow-Group 144B. Color (when fully mature): upper surface: near Green Group 137C. under surface: near Green Group 138B.

Inflorescence:

*Number of flowers*.—Commonly approximately 5 to 36 blooms on average in a cluster, and approximately 150 blooms on a plant at a given time.

*Peduncle*.—Near Yellow-Green Group 144A in coloration, commonly approximately 2 cm in length, and commonly covered with short pubescence having a length of approximately 1 mm.

*Sepals*.—Upper surface: covered with short pubescence, and commonly near Green Group 138B in coloration. under surface: generally smooth, and near Yellow-Green Group 144A in coloration. Size: commonly approximately 1 cm in length on average, and approximately 5 mm in width at the base. Number: five.

*Buds*.—Shape: generally ovoid. Length: approximately 1 cm on average at the calyx breaks. Diameter: approximately 6 mm on average as the calyx breaks. Color: near Red-Purple Group 59B when opening.

*Flower*.—Form: cup-like, single. Diameter: approximately 3.2 cm on average when fully open. Color (when opening): upper surface: commonly a blend of Red-Purple Group 57A and Red-Purple Group 60A with Red-Purple Group 65C at the base. under surface: near Red-Purple Group 60B with Red-Purple Group 65C at the base. Color (at end of blooming): upper surface: near Red-Purple Group 57B with White Group 155A at the base. under surface: near Red-Purple Group 57C with White Group 156A at the base. Fragrance: none noticeable. Petal number: commonly approximately 5 on average under normal growing conditions. Petal length: commonly approximately 2 cm on average. Petal width: commonly approximately 1.8 cm on average. Petal shape: obcordate. Petal margin: entire. Petal apex: obcordate. Petal base: broadly cuneate. Petal drop: good, the petals commonly detach cleanly and freely drop upon full maturity. Stamen number: approximately 71 on average. Anthers: Yellow-Orange Group 17A in coloration. Filaments: approximately 4 mm in length, and the coloration is near Red-Purple Group 63C with White Group 155A at the base. Pollen: Yellow-Orange Group 17A in coloration. Pistils: commonly clustered together, and commonly number approximately 13 on average. Styles: commonly approximately 2 mm in length, approximately 1 mm in width and near Green Group 139D in coloration. Stigma: approximately 1 mm in size, and Green Group 142D in coloration. Receptacle: commonly spherical in shape, approximately 3 mm in diameter, smooth in texture, near Yellow-Green Group 144A in coloration, with achenes commonly being present of the bottom and wall.

Development:

*Vegetation*.—Vigorous and strong.

*Blossoming*.—Abundant.

*Resistance to diseases*.—Typical of the type.

*Hip formation*.—Sparse.

*Hardiness*.—U.S.D.A. Hardiness Zone Nos. 5 to 9.

Plants of the 'Harpballred' variety have not been observed under all possible environmental conditions to date. Accordingly, it is possible that the phenotypic expression may vary somewhat with changes in light intensity and duration, cultural practices, and other environmental conditions.

I claim:

1. A new and distinct Shrub rose plant characterized by the following combination of characteristics:

(a) abundantly forms in clusters attractive small single cup-like bright red blossoms with a white eye that drop their petals well upon full maturity, (b) exhibits a mounding growth habit, (c) forms vigorous vegetation, (d) forms attractive dark green foliage with a glossy upper surface, and (e) is well suited for growing as attractive ornamentation in the landscape;

substantially as herein shown and described.

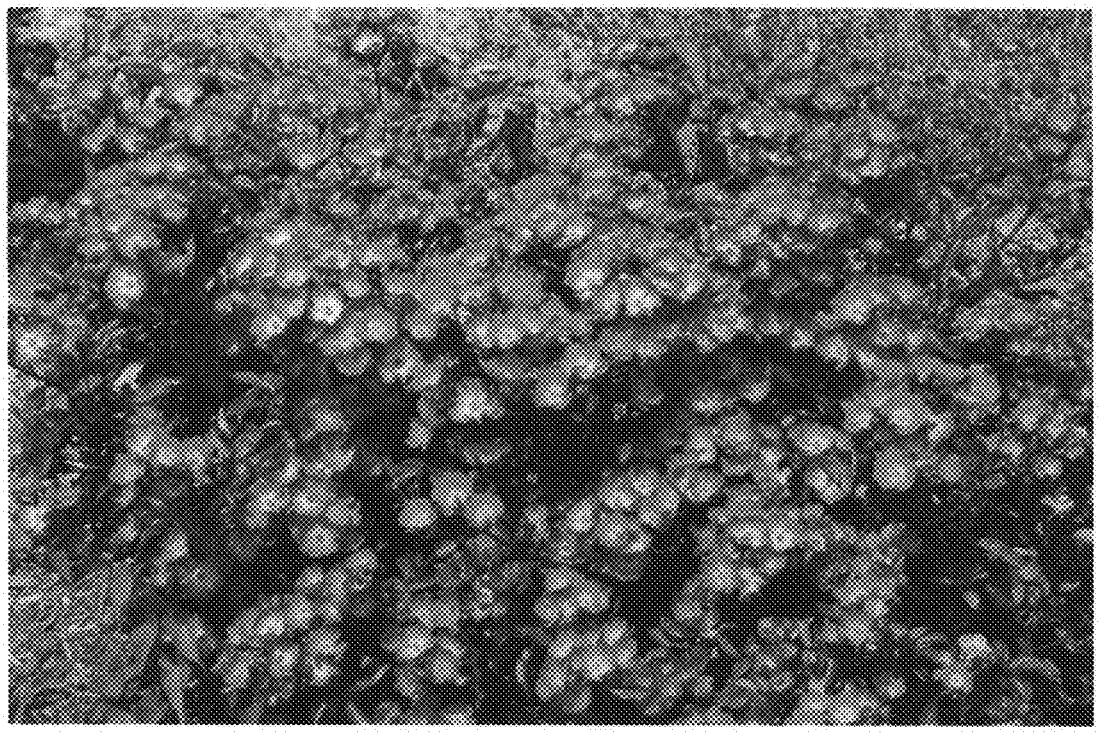

* * * * *